United States Patent
Montalvo et al.

(10) Patent No.: US 11,571,285 B2
(45) Date of Patent: Feb. 7, 2023

(54) EVACUATION DAM FRAME

(71) Applicant: Loma Linda University, Loma Linda, CA (US)

(72) Inventors: Abraham Montalvo, Corona, CA (US); Jessica Kim, Redlands, CA (US); Joseph Caruso, Morro Bay, CA (US); Seth Myhre, Beaumont, CA (US); Roberto Savignano, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

(21) Appl. No.: 17/016,181

(22) Filed: Sep. 9, 2020

(65) Prior Publication Data
US 2022/0071748 A1 Mar. 10, 2022

(51) Int. Cl.
*A61C 17/08* (2006.01)
*A61C 17/12* (2006.01)

(52) U.S. Cl.
CPC .............. *A61C 17/08* (2019.05); *A61C 17/12* (2019.05)

(58) Field of Classification Search
CPC .................................. A61C 17/08; A61C 17/12
USPC .......................................................... 433/96
See application file for complete search history.

(56) References Cited

U.S. PATENT DOCUMENTS

| | | | |
|---|---|---|---|
| 485,609 A | 11/1892 | Casebeer | |
| 1,930,712 A * | 10/1933 | Girvin | A61C 17/08 433/136 |
| 2,507,938 A * | 5/1950 | Smith | A61C 19/001 433/94 |
| 3,080,864 A | 3/1963 | Berman | |
| 3,396,468 A * | 8/1968 | Dayhoff | A61C 17/08 433/140 |
| 3,631,598 A * | 1/1972 | Lussier | A61C 17/08 433/31 |
| 3,735,491 A * | 5/1973 | Pabalan, Jr. | A61C 17/10 433/93 |
| 3,772,790 A * | 11/1973 | Swan-Gett | A61B 1/24 433/136 |
| 3,781,994 A * | 1/1974 | Hesselgren | A61C 5/82 433/137 |
| 3,850,168 A | 11/1974 | Ferguson et al. | |

(Continued)

FOREIGN PATENT DOCUMENTS

| | | | |
|---|---|---|---|
| EM | 001035414-0001 | 12/2008 | |
| IN | 331533-001-0001 | 9/2020 | |
| WO | WO-2010089486 A3 * | 9/2010 | ............. A61C 5/122 |

OTHER PUBLICATIONS

Intraoral vs. Extraoral Suction Devices; A review of the effectiveness of equipment on capturing aerosols; Jun. 2, 2020; https://www.aaoms.org/docs/COVID-19/Intraoral_vs_Extraoral_Suction_Devices.pdf.

(Continued)

*Primary Examiner* — Matthew M Nelson
(74) *Attorney, Agent, or Firm* — Polsinelli PC

(57) ABSTRACT

An evacuation dam apparatus including a frame having a top frame member, a bottom frame member, and two side frame members. A working area formed by the frame, a plurality of ports adjacent the working area, an outlet fluidly coupled with the plurality of ports. A fluid flow from at least a portion of the plurality of ports to the outlet forms a fluid flow path across the working area and at least a portion of the fluid flow path is formed within the frame.

18 Claims, 12 Drawing Sheets

(56) References Cited

U.S. PATENT DOCUMENTS

| | | | | |
|---|---|---|---|---|
| 4,053,984 A * | 10/1977 | Moss | A61C 17/10 | 433/140 |
| 4,167,814 A * | 9/1979 | Schubert | A61C 17/08 | 433/93 |
| 4,240,789 A * | 12/1980 | Rosenthaler | A61C 17/08 | 433/136 |
| 4,261,697 A * | 4/1981 | Newitter | A61C 5/82 | 433/137 |
| 4,417,874 A * | 11/1983 | Andersson | A61C 17/08 | 433/96 |
| D287,402 S | 12/1986 | Orsing | | |
| 4,664,628 A * | 5/1987 | Totaro | A61C 17/08 | 433/136 |
| 4,695,253 A * | 9/1987 | Tysse | A61C 5/82 | 433/136 |
| 4,889,490 A | 12/1989 | Jenkinson | | |
| 4,944,310 A | 7/1990 | Sullivan | | |
| 5,015,243 A * | 5/1991 | Schifano | B08B 15/007 | 604/315 |
| 5,071,347 A * | 12/1991 | McGuire | A61C 17/08 | 433/91 |
| 5,104,315 A * | 4/1992 | McKinley | A61C 17/0211 | 433/80 |
| 5,127,411 A * | 7/1992 | Schoolman | A61C 17/06 | 433/91 |
| 5,279,599 A * | 1/1994 | Wilk | A61M 25/007 | 604/313 |
| 5,299,599 A | 4/1994 | Farmer et al. | | |
| 5,516,286 A * | 5/1996 | Kushner | A61C 5/90 | 433/136 |
| 5,547,375 A * | 8/1996 | Schneider | A61C 17/08 | 433/96 |
| 5,868,722 A * | 2/1999 | Yeh | A61B 18/00 | 604/313 |
| 5,931,673 A * | 8/1999 | Bolbolan | A61C 5/82 | 433/136 |
| 5,941,873 A * | 8/1999 | Korenfeld | A61F 9/008 | 606/4 |
| D418,918 S | 1/2000 | Cunningham | | |
| 6,135,770 A * | 10/2000 | Bembenek | A61C 5/82 | 433/136 |
| 6,267,591 B1 * | 7/2001 | Barstow | A61C 17/08 | 433/140 |
| D449,376 S | 10/2001 | McDonald et al. | | |
| D449,883 S | 10/2001 | McDonald et al. | | |
| 6,406,447 B1 * | 6/2002 | Thrash | A61M 3/0287 | 604/176 |
| 6,663,610 B1 * | 12/2003 | Thompson | A61M 1/84 | 604/128 |
| 6,763,832 B1 | 7/2004 | Kirsch et al. | | |
| 6,942,650 B1 * | 9/2005 | Schultz | B01D 46/24 | 604/315 |
| D515,697 S | 2/2006 | Nakamura et al. | | |
| 7,207,977 B2 * | 4/2007 | Thompson | A61M 1/84 | 604/35 |
| 7,261,560 B2 * | 8/2007 | Abo | A61C 17/08 | 433/91 |
| D578,642 S | 10/2008 | White et al. | | |
| D607,993 S | 1/2010 | Cowan | | |
| D636,880 S | 4/2011 | Osborn | | |
| 8,585,403 B2 * | 11/2013 | Ames | A61C 17/08 | 433/96 |
| 8,708,985 B2 * | 4/2014 | Schultz | A61M 1/85 | 604/319 |
| D802,746 S | 11/2017 | Ocklenburg et al. | | |
| D843,561 S | 3/2019 | Bonato et al. | | |
| 10,245,175 B2 * | 4/2019 | Podmore | A61M 1/742 | |
| D862,686 S | 10/2019 | Mohamed | | |
| D884,159 S | 5/2020 | Moon et al. | | |
| 10,765,497 B2 * | 9/2020 | Maycher | A61M 25/02 | |
| 10,952,831 B1 * | 3/2021 | Dürrstein | A61C 17/092 | |
| 10,959,820 B1 * | 3/2021 | Steele | A61C 17/10 | |
| 11,179,287 B1 * | 11/2021 | Mirbahaeddin | A61B 90/05 | |
| D942,617 S | 2/2022 | Smith | | |
| 2003/0134253 A1 | 7/2003 | Hirsch et al. | | |
| 2004/0209224 A1 * | 10/2004 | Heasley | A61C 5/82 | 433/139 |
| 2005/0037315 A1 * | 2/2005 | Inoue | A61C 17/0211 | 433/91 |
| 2006/0008764 A1 * | 1/2006 | Abo | A61C 17/08 | 433/91 |
| 2006/0252006 A1 * | 11/2006 | Apelker | A61C 5/90 | 433/136 |
| 2012/0009861 A1 | 1/2012 | Mercey et al. | | |
| 2012/0199135 A1 * | 8/2012 | Podmore | A61M 16/0493 | 128/848 |
| 2013/0095450 A1 * | 4/2013 | Ames | A61C 17/08 | 433/96 |
| 2017/0056143 A1 * | 3/2017 | Hyun | A61C 17/024 | |
| 2017/0087004 A1 * | 3/2017 | Podmore | A61M 16/0495 | |
| 2019/0269312 A1 * | 9/2019 | Hines | A61B 1/32 | |
| 2020/0405988 A1 * | 12/2020 | Flint | A61C 17/10 | |
| 2021/0338377 A1 * | 11/2021 | Ferone | A61C 17/08 | |
| 2021/0346134 A1 | 11/2021 | Reingold | | |
| 2021/0378804 A1 * | 12/2021 | Renne | A61B 1/24 | |
| 2022/0071748 A1 * | 3/2022 | Montalvo | A61B 90/40 | |

OTHER PUBLICATIONS

Rajeev, Karthika & Kuthiala, Parnika & Ahmad, Faisal & Tafadar, Nazamuddin & Ganorkar, Onkar & Voulligonda, Dheeraj & Vinay, Rahul & Tiwari, Chandra. (2020). Review Article Aerosol Suction Device: Mandatory Armamentarium in Dentistry Post Lock Down. vol. 8.

[Evaluation of the spatter-reduction effectiveness and aerosol containment of eight dry-field isolation techniques], quintpub.com, by [Theodore D. Ravenel et al.], Posted: Sep. 2020 [online], site visited: [Apr. 28, 2022], URL: <http://www.quintpub.com/userhome/qi/qi_51_8_ravenel_p660.pdf>. (Year: 2020).

[Henry Schein Announces New Proprietary Single-Use Aerosol Evacuator], aegisdentalnetwork.com, Posted: Jul. 14, 2021 [online], site visited: [Apr. 28, 2022], URL: <https://www.aegisdentalnetwork.com/news/2021/07/14/henry-schein-announces-new-proprietary-single-use-aerosol-evacuator>. (Year: 2021).

[Aerosol and spatter mitigation in dentistry: Analysis of the effectiveness of 13 setups], wileyonlinelibrary.com, by [John C. Comisi et al.], Published: [Jan. 19, 2021] [online], site visited: [Apr. 28, 2022], URL: <https://onlinelibrary.wiley.com/doi/epdf/10.1111/jerd.12717>. (Year: 2021).

International Search Report and Written Opinion for International application No. PCT/US2021/049733, dated Dec. 23, 2021, 11 pages.

* cited by examiner

EVACUATION DAM FRAME

BACKGROUND

1. Field of the Invention

The present inventive concept relates generally to an evacuation frame for use in dental and/or medical applications.

2. Description of Related Art

Dental procedures often generate aerosolized particle or droplets and may involve a rubber dam to isolate a procedure area and reduce contamination of the procedure site. However, particles including water droplets, saliva, dental compounds, and/or the like can be introduced into the immediate atmosphere and interfere with the procedure. A patient and/or a dental professional may be exposed to these particles including a patient's germs and/or bodily fluids.

SUMMARY

An evacuation dam apparatus comprising a frame having a top frame member, a bottom frame member, and two side frame members. The frame forming a working area and a plurality of ports adjacent the working area with an outlet fluidly coupled with the plurality of ports. The evacuation dam is adapted to provide a fluid flow from at least a portion of the plurality of ports to the outlet to form a fluid flow path across the working area and at least a portion of the fluid flow path is formed within the frame.

The plurality of ports can include at least one positive flow outlet port and at least one negative flow inlet port.

An inlet can be configured to receive a positive pressure flow, the inlet fluidly configured with the at least one positive flow outlet port, and the outlet configured to receive a negative pressure flow fluidly coupled with the at least one negative flow inlet port.

The fluid flow path can extend from plurality of positive flow outlet ports to the plurality of negative flow inlet ports.

The at least one positive flow outlet port can be directional and/or substantially aligned with the at least one negative flow port. The at least one negative flow port can include a convex collection area disposed around at least a portion thereof.

The frame can include a plurality of posts extending away from the working area. The plurality of posts can have a barb formed on a distal end.

The frame can have an eye protection coupler disposed thereon, the eye protection coupler can be configured to receive at least a portion of an eye protection apparatus. The top frame member can be slidingly engaged with the side members. The outlet can be slidingly engaged with the bottom frame member.

An evacuation dam system can include an evacuation dam having a frame including a top frame member, a bottom frame member, and two side frame members. A working area defined by the frame; positive flow inlet port configured to receive a positive pressure airflow therein; a positive flow outlet port adjacent the working area and fluidly coupled with the positive flow inlet port. A negative flow inlet port adjacent the working area; a negative flow outlet port configured to receive negative pressure airflow therein, the negative flow outlet port fluidly couple with the negative flow inlet port. The evacuation dam system is configured to provide a fluid flow from at least the positive flow outlet port to the negative flow inlet port to form a fluid flow path across the working area. At least a portion of the fluid flow path is formed within an interior of the frame.

A positive pressure fluid flow path can be formed in the top frame member. A negative pressure fluid flow path can be formed in the bottom frame member.

The at least one negative flow port can include a convex collection area disposed around at least a portion thereof.

The convex collection area can be coupled with the bottom frame member and can be vertically displaceable relative to the bottom frame member.

An eye protection coupler can be configured to receive at least a portion of an eye protection apparatus, the eye protection coupler disposed on at least a portion of the frame.

A saliva suction holder can be coupled with a side frame member. The saliva suction holder can be displaceable along a longitudinal length of the side frame member.

The top frame member can be slidingly displaceable along a longitudinal length of the side frame member, wherein changing a longitudinal length of the working area.

BRIEF DESCRIPTION OF THE DRAWINGS

The novel features of the disclosure are set forth with particularity in the appended claims. A better understanding of the features and advantages of the present inventive concept will be obtained by reference to the following detailed description that sets forth illustrative examples, in which the principles of the disclosure are utilized, and the accompanying drawings of which:

DETAILED DESCRIPTION

Figure 1:
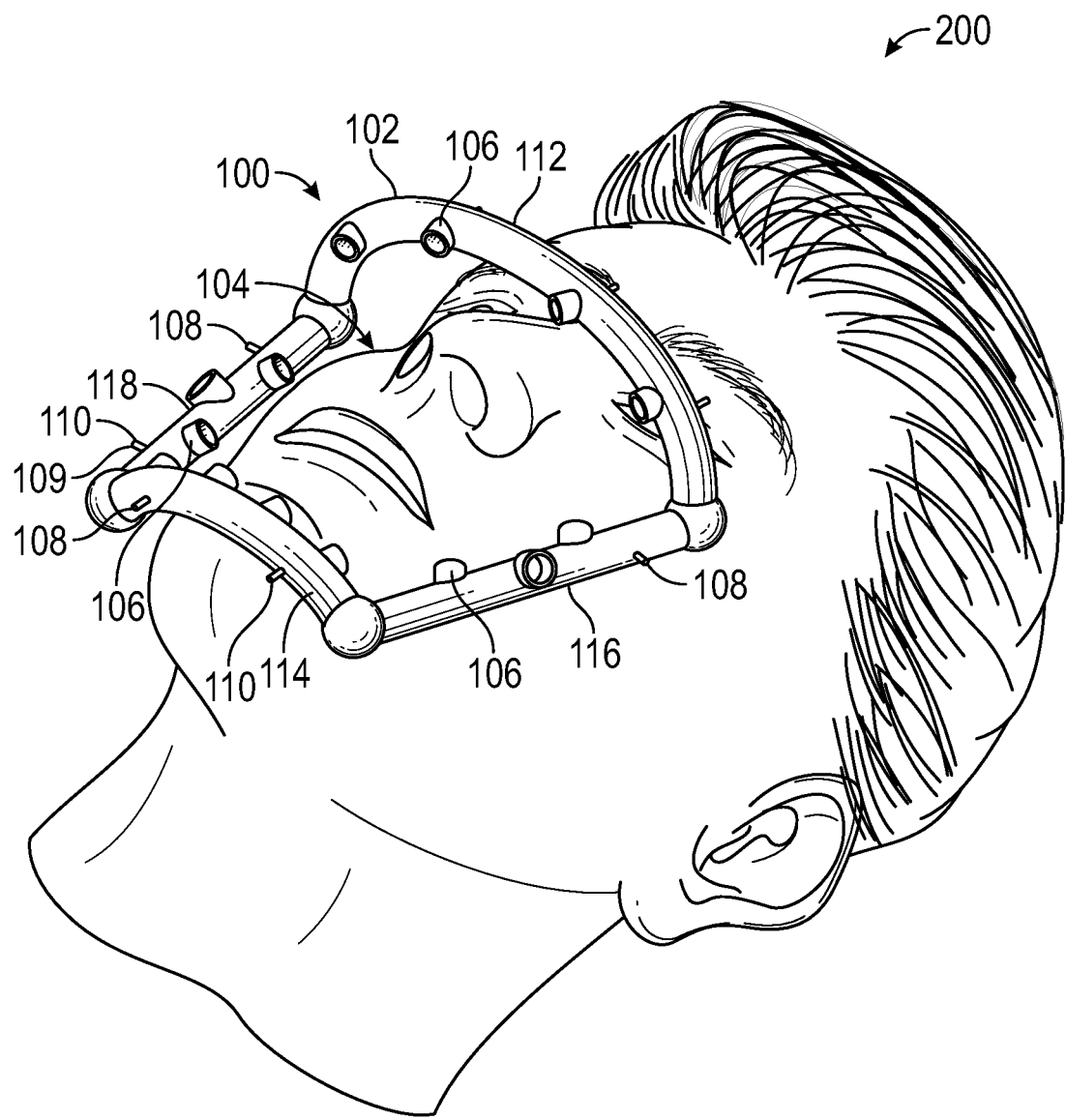
FIG. 1 is a diagrammatic view of an evacuation dam, according to at least one embodiment of the present inventive concept.

Examples and various features and advantageous details thereof are explained more fully with reference to the exemplary, and therefore non-limiting, examples illustrated in the accompanying drawings and detailed in the following description. Descriptions of known starting materials and processes can be omitted so as not to unnecessarily obscure the disclosure in detail. It should be understood, however, that the detailed description and the specific examples, while indicating the preferred examples, are given by way of illustration only and not by way of limitation. Various substitutions, modifications, additions and/or rearrangements within the spirit and/or scope of the underlying inventive concept will become apparent to those skilled in the art from this disclosure.

I. Terminology

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited only those elements but can include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term substantially, as used herein, is defined to be essentially conforming to the particular dimension, shape or other word that substantially modifies, such that the component need not be exact. For example, substantially cylindrical means that the object resembles a cylinder, but can have one or more deviations from a true cylinder.

Additionally, any examples or illustrations given herein are not to be regarded in any way as restrictions on, limits to, or express definitions of, any term or terms with which they are utilized. Instead these examples or illustrations are to be regarded as being described with respect to one particular example and as illustrative only. Those of ordinary skill in the art will appreciate that any term or terms with which these examples or illustrations are utilized encompass other examples as well as implementations and adaptations thereof which can or cannot be given therewith or elsewhere in the specification and all such examples are intended to be included within the scope of that term or terms. Language designating such non-limiting examples and illustrations includes, but is not limited to: "for example," "embodiment," "for instance," "e.g.," "In some examples," and the like.

Although the terms first, second, etc. can be used herein to describe various elements, components, regions, layers and/or sections, these elements, components, regions, layers and/or sections should not be limited by these terms. These terms are only used to distinguish one element, component, region, layer or section from another. Thus, a first element, component, region, layer or section discussed below could be termed a second element, component, region, layer or section without departing from the teachings of the present inventive concept.

II. General Architecture

The systems and methods disclosed herein relate to an evacuation dam. While the present disclosure illustrates an evacuation dam drawn to dental applications, it is within the scope of the present disclosure to encompass medical procedures and/or medical settings that would benefit from a controlled field with laminar flow and evacuation. The evacuation dam can be positioned over a portion of dental patient's face and provide a directional flow to reduce and/or eliminate particulate distribution during a dental procedure. The evacuation dam and/or evacuation dam frame of the present disclosure can be formed via additive manufacturing (e.g. 3-D printing), injection molded, cast, extruded, and/or other process. The evacuation dam and/or evacuation dam frame can be formed of metals, alloys, plastics, rubber, resins, fiber boards, combinations thereof, and/or similar materials having suitable rigidity to maintain the evacuation dam and/or evacuation dam frame.

The evacuation dam and/or evacuation dam frame can be disposable for each patient and/or the evacuation dam and/or evacuation dam frame can be reusable and sterilized between patients using one or more of cleaning solutions and/or ultraviolet light sources.

The presently disclosed technology may be implemented in dental, medical, and/or other related field and can further be implemented with or without a rubber dam. The presently disclosed technology may be implemented to improve patient experience, improve working area cleanliness for medical professionals, and/or maintain a sanitary environment.

FIG. 1 illustrates an environmental view of an evacuation dam, according to at least one embodiment of the present disclosure. An evacuation dam 100 can be operable to be positioned and/or arranged over a portion of a patient 200. While the evacuation dam 100 of the present disclosure is described with respect to dental procedures, and thus positioned and/or arranged over the mouth of the patient 200, it is within the scope of the present disclosure to implement the evacuation dam 100 with other medical procedures in which the evacuation dam 100 can be positioned over other portions of the patient 200.

The evacuation dam 100 can be sized relative to the patient 200 including, but not limited to, fixed sizing determine based on one or more features of the patient 200 and/or customized and/or adjusted in one or more directions to accommodate one or more features of the patient. At least one instance of a customizable and/or adjustable evacuation dam system is described with respect to FIG. 10.

The evacuation dam 100 can have a frame 102 formed around and at least substantially encompassing a working area 104. The frame 102 can allow fluid flow through at least a portion thereof, thereby allowing evacuation across the working area 104. The frame 102 can have a plurality of ports 106 disposed thereon, and operable to receive positive pressure and/or negative pressure flow. The plurality of ports 106 can be operably arranged within the frame 102 adjacent to the working area 104 and operable to form a fluid flow path across the working area 104 either via positive pressure (e.g. forced air), negative pressure (e.g. vacuum), and/or combinations thereof.

The evacuation dam 100 can also include a plurality of posts 108 extending from the frame 102 away from the working area 104. The plurality of posts 108 can be operable to receive a rubber dam (not shown) and secure the rubber dam to the frame 102. The plurality of posts 108 can be uniformly shaped cylinders, squares, hexagons, and/or other shapes. In at least one embodiment, the plurality of posts 108 includes a barb 109 at the distal end 110. The barb 109 can prevent the rubber dam from becoming incidentally decoupled from the frame 102.

The frame 102 can be formed from one or more individual elements including, but not limited to, a top frame member 112, a bottom frame members 114, and/or side frame members 116, 118. The top frame member 112, bottom frame member 114, and/or the side frame members 116, 118 can collectively form and define the working area 104. The plurality of ports 106 and/or the plurality of posts 108 can be formed on any one of and/or any combination of the top frame member 112, bottom frame member 114, and/or the side frame members 116, 118.

Figure 2:
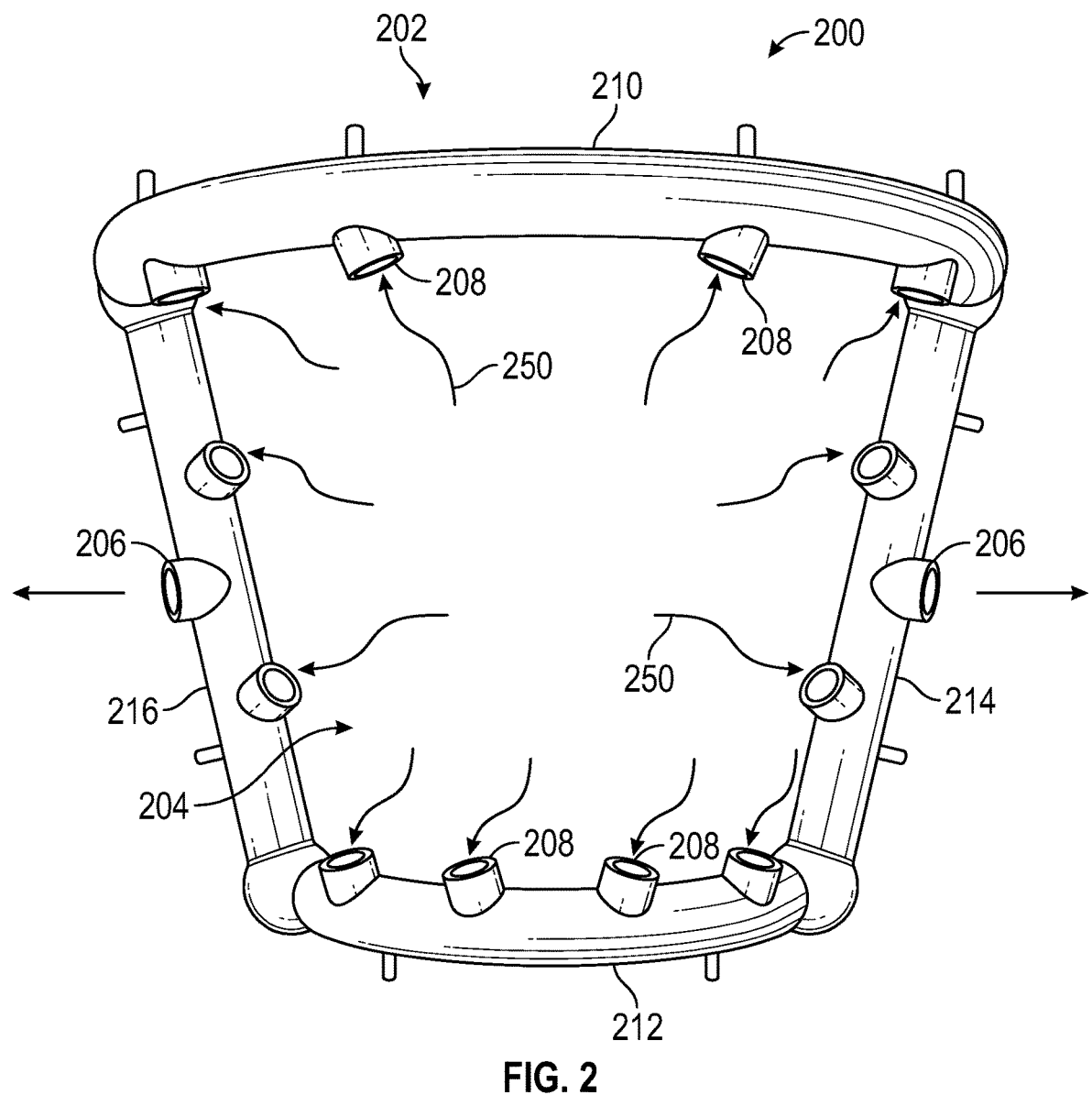
FIG. 2 is a top diagrammatic view of an evacuation dam with negative flow, according to at least one embodiment of the present inventive concept.

FIG. 2 illustrates a negative flow evacuation dam, according to at least one embodiment of the present disclosure. An evacuation dam 200 can have a frame 202 operably defining a working area 204. The evacuation dam 200 can be operably arranged for a negative pressure flow, generating an evacuation and/or vacuum across the working area 204, thus reducing particles generated during a procedure. The particles can include, but are not limited to, water droplets, saliva, tooth fragments, blood, and/or the like.

The frame 202 can have one or more outlet ports 206 and one or more inlet ports 208. The one or more outlet ports 206 can be operable to couple with an evacuation (e.g. vacuum) line. In at least one embodiment, the evacuation line can be a standard suction line integrated with a dental chair. The one or more inlet ports 208 can be fluidly coupled (through an interior of the frame 202) with the one or more outlet ports 206. The one or more inlet ports 208 are operably arranged to pull a negative flow across the working area 204, thereby evacuating the working area 204. In at least one embodiment, the one or more inlet ports 208 can distribute the negative pressure flow generated by the one or more outlet ports 206.

As can be appreciated in FIG. 2, the one or more inlet ports 208 can be substantially evenly distributed along the frame 202 adjacent to the working area 204. While FIG. 2 illustrates a top frame member 210 and a bottom frame member 212 having four inlet ports 208 and each side frame member 214, 216 having three frame members, it is within the scope of this disclosure to implement any number of inlet ports 208 on the frame 202 to provide sufficient evacuation. The one or more inlet ports 208 can generate a substantially turbulent evacuation flow 250 across the working area 204 depending on the negative pressure flow connected to the one or more outlets 206.

The flow path generated by the evacuation dam 200 can travel from the one or more inlets 208 through at least a portion of the frame 202 and to a corresponding one of the one or more outlets 206. Depending on the arrangement of the one or more outlets 206, the one or more inlets 208, and/or the frame 202, the frame 202 can have one or more flow paths therein and can include solid portions providing flow therethrough. The solid portions can provide structural rigidity to the frame 202 and/or direct fluid flow through the frame 202.

Figure 3:
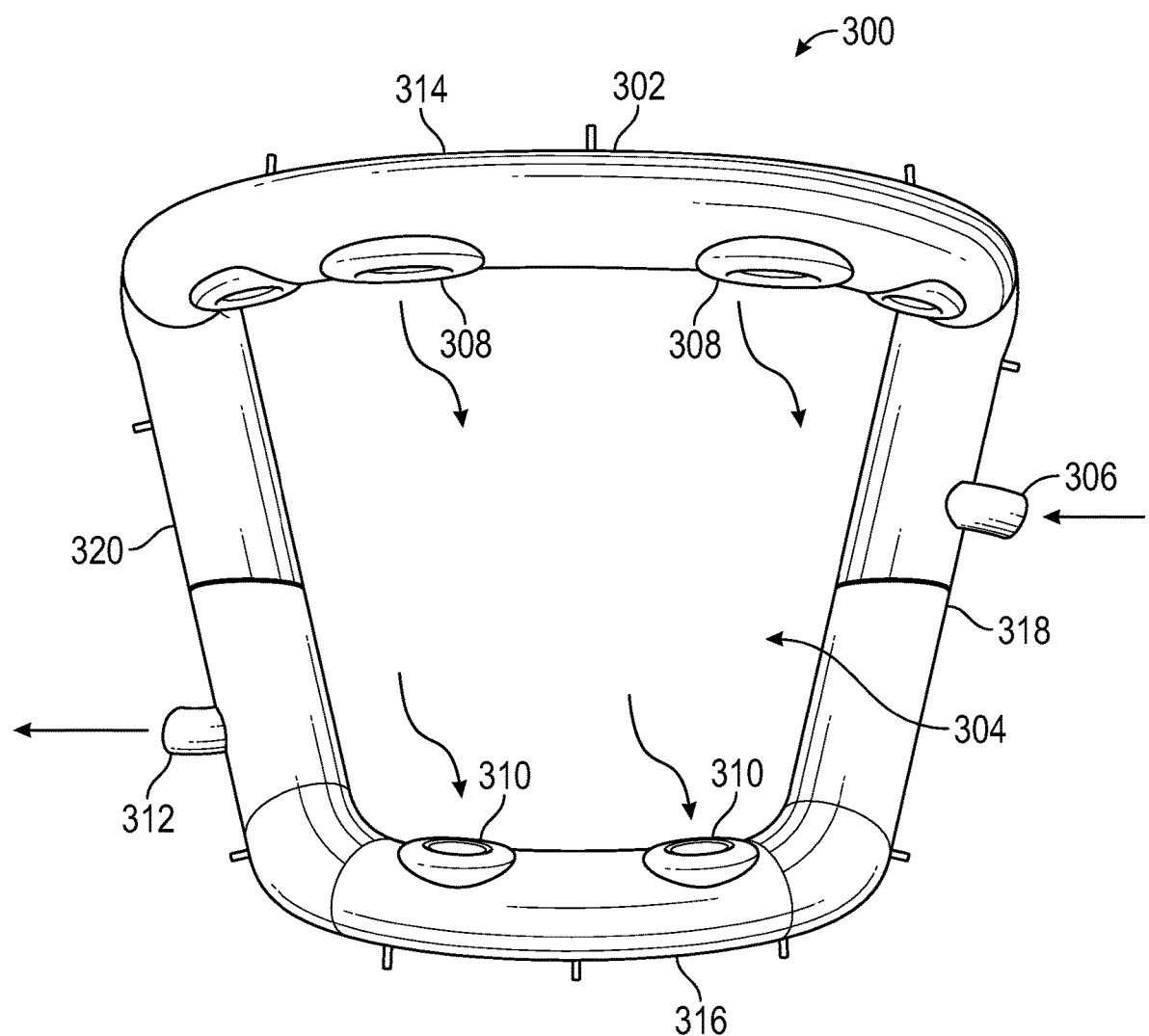
FIG. 3 is a top diagrammatic view of an evacuation dam with negative flow and positive flow, according to at least one embodiment of the present inventive concept.

FIG. 3 illustrates a dual flow evacuation dam, according to at least one embodiment of the present disclosure. An evacuation dam 300 can have a frame 302 operably defining a working area 304. The evacuation dam 300 can be operably arranged for a directional flow across the working area 304 utilizing a combination of positive and negative flows, thereby generating an evacuation and/or vacuum across the working area 304.

The frame 304 can have a positive flow inlet port 306 and one or more positive flow outlet ports 308. The positive flow inlet port 306 can be operable to receive a positive pressure airflow connection therein and distribute the positive pressure airflow across the one or more positive flow outlet ports 308. The one or more positive flow outlet ports 308 can be arranged along at least one side of the frame 302 and adjacent to the working area 304. The positive flow inlet port 306 can be fluidly coupled (through an interior of the frame 302) with the one or more positive flow outlet ports 308.

The evacuation dam 300 can include one or more negative flow inlet ports 310 operably arranged along at least one side of the frame 302 and adjacent to the working area 304. At least one negative flow outlet ports 312 can be operable to couple with an evacuation (e.g. vacuum) line and be fluidly coupled with the one or more negative flow inlet ports 310. The one or more negative flow inlet ports 310 can be fluidly coupled (through an interior of the frame 302) with the at least one negative flow outlet ports 312. In at least one embodiment, the evacuation line can be a standard suction line integrated with a dental chair.

The one or more positive flow outlet ports 308 and the one or more negative flow inlet ports 310 collectively induce an evacuation across the working area 304. The one or more inlet ports 310 are operably arranged to pull a negative flow across the working area 304 while the one or more positive flow outlet ports 308 are operably to push a positive flow across the working area 304.

As can be appreciated in FIG. 3, the one or more positive flow outlet ports 308 can be substantially evenly distributed along a top frame member 314 and adjacent to the working area 304, while the one or more negative flow inlet ports 310 can be substantially evenly distributed along a bottom frame member 316 and adjacent to the working area 304. While FIG. 3 illustrates a top frame member 314 and a bottom frame member 316 having the one or more positive flow outlet ports 308 and the one or more negative flow inlet ports 314, respectively, it is within the scope of this disclosure to implement the one or more positive flow outlet ports 308 and the one or more negative flow inlet ports 314 on any portion of the frame 302 including the top frame member 314, the bottom frame member 316, and/or the side frame members 318, 320. Further, it is within the scope of this disclosure to implement any number of positive flow outlet ports 308 and/or negative flow inlet ports 310 on the frame 302 to provide sufficient evacuation.

Figure 4:
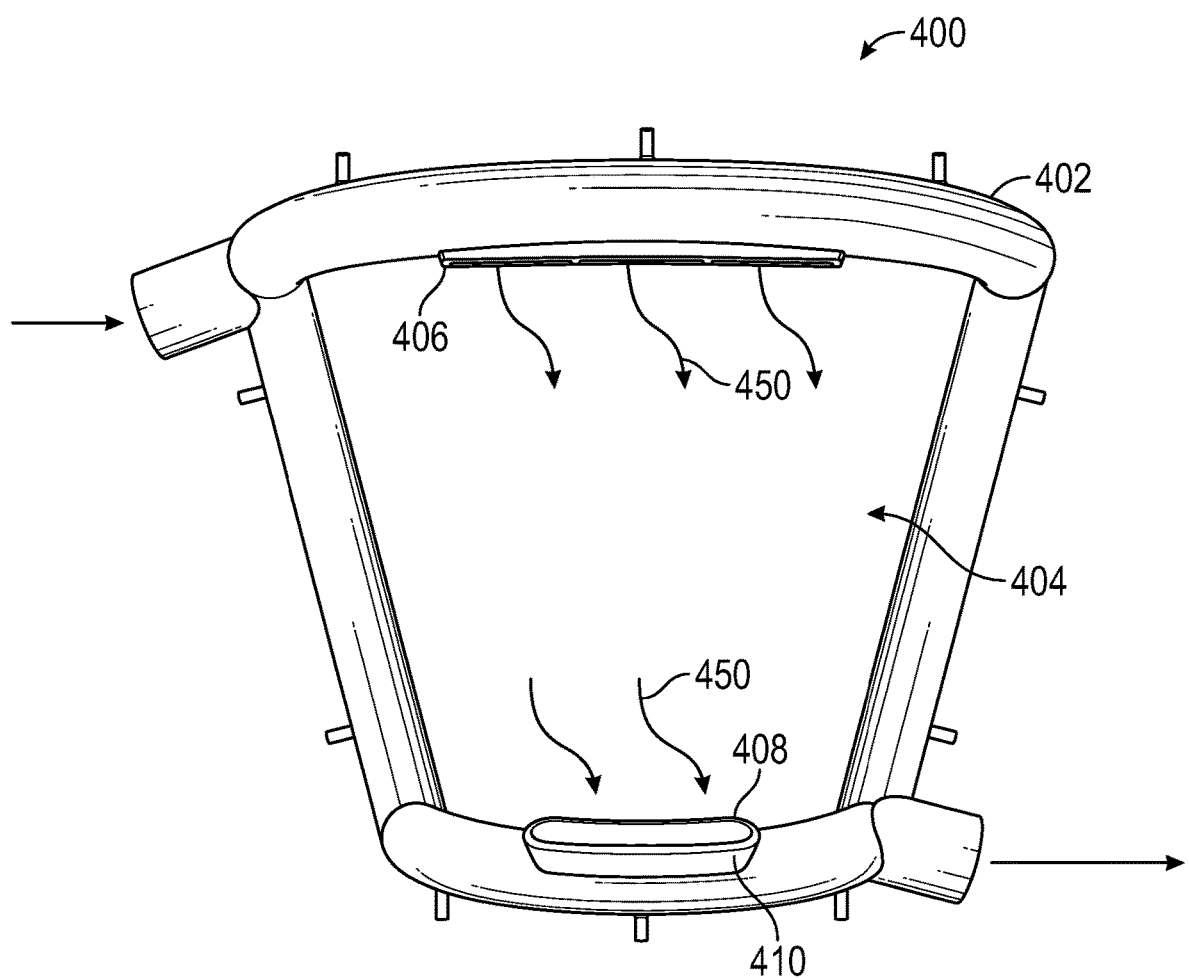
FIG. 4 is a top diagrammatic view of an evacuation dam with a turbulent negative flow and turbulent positive flow, according to at least one embodiment of the present inventive concept.

FIG. 4 illustrates a dual flow evacuation dam having a directional positive flow and a dished negative flow inlet, according to at least one embodiment of the present disclosure. The evacuation dam 400 have a frame 402 defining a working area 404 with one or more positive flow outlet ports 406 operably disposed on the frame 402 and arranged adjacent to the working area 404. The one or more positive flow outlet ports 406 can be positioned directionally to substantially align with one or more negative flow inlet ports 408. As can be appreciated in FIG. 4, the one or more negative flow inlet ports 408 can include a convex, or dished, collection area 410 increase the capture of particles within the working area 404.

The substantially directionally aligned one or more positive flow outlet ports 406 and/the convex collection area 410 of the one or more negative flow inlet ports 408 can produce a substantially laminar flow path 450 across the working area 404, thereby increasing capture of particles within the working area 404.

Figure 5:
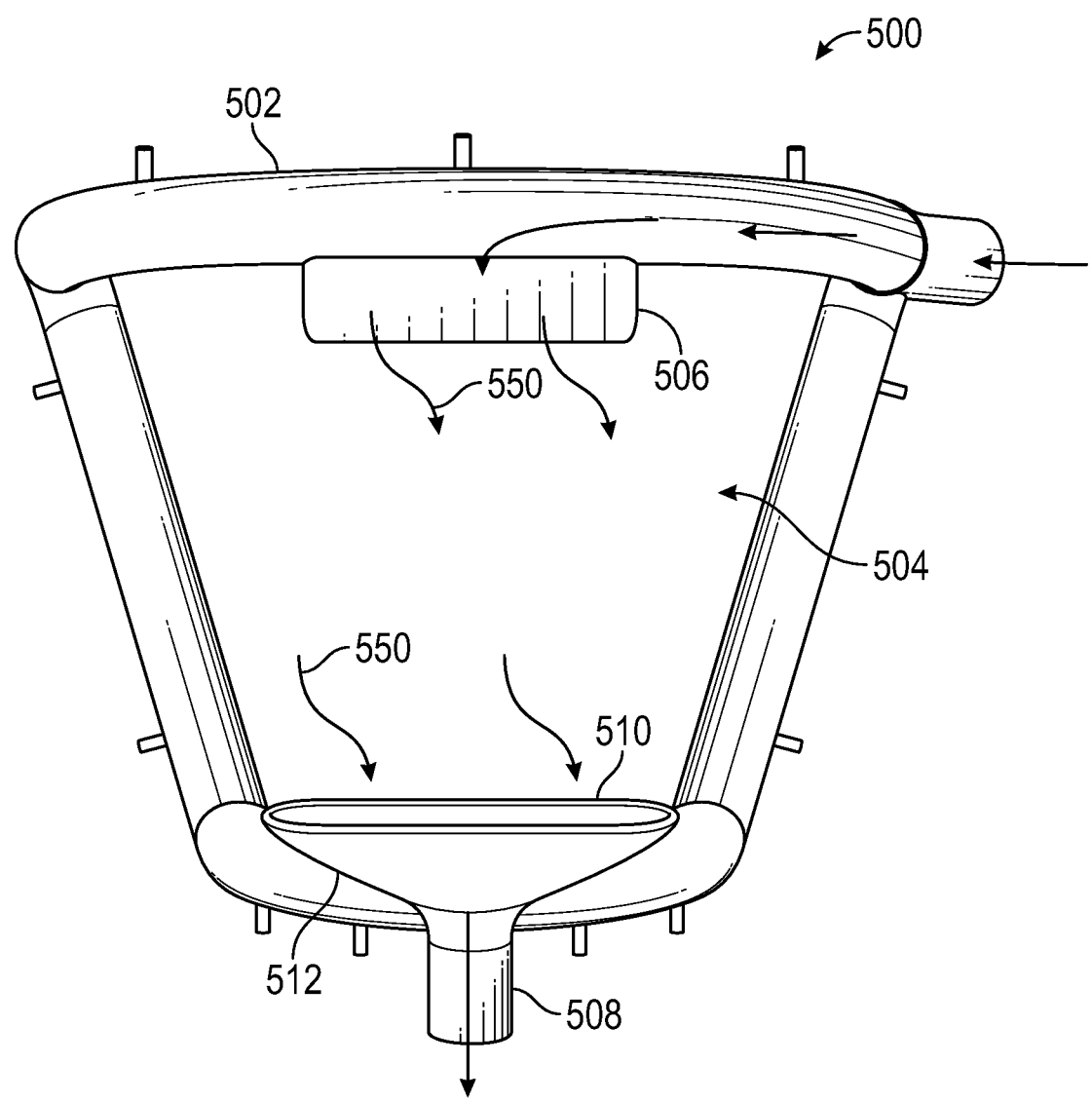
FIG. 5 is a top diagrammatic view of an evacuation dam with a laminar negative flow and a laminar positive flow, according to at least one embodiment of the present inventive concept.

FIG. 5 illustrates a dual flow evacuation dam having a splashguard 506 and a centralized evacuation connection, according to at least one embodiment of the present disclosure. The evacuation dam 500 can include a splashguard 506 coupled with the frame 502. The splashguard 506 can extend a predetermined distance into the working area 504 to prevent particles, moisture, and/or saliva that are not captured by the evacuation dam 500 from contacting a patient's face or skin.

The evacuation dam 500 can also include a central evacuation connection 508 operable to align the central evacuation connection 508 with one or more negative flow inlet ports 510. Alignment between the central evacuation connection 508 and the one or more negative flow inlet ports 510 creates an aligned flow path 550 which can reduce noise and improve performance. The convex collection area 512 and the central evacuation connection 508 can be coupled with the frame 502, thus eliminating the flow path of the negative flow through frame which can increase the ability for sanitization and/or cleaning. In at least one embodiment, the convex collection area 512 and/or the central evacuation connection 508 can be pivoted relative to the frame to adjust the flow path 550 and maximize evacuation of the evacuation dam 500.

Figure 6:
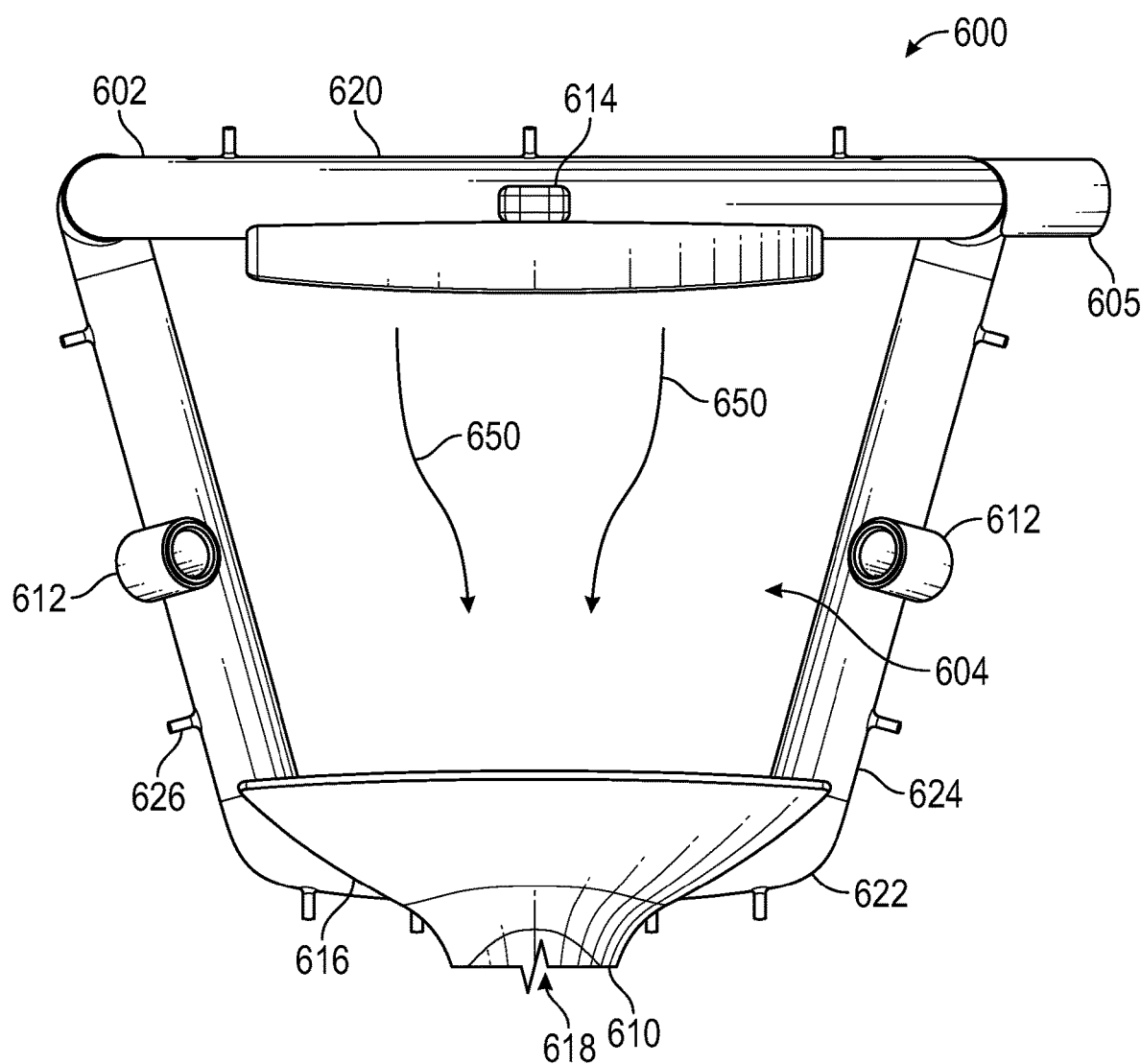
FIG. 6 is a top diagrammatic view of an evacuation dam system, according to at least one embodiment of the present inventive concept.
Figure 7:
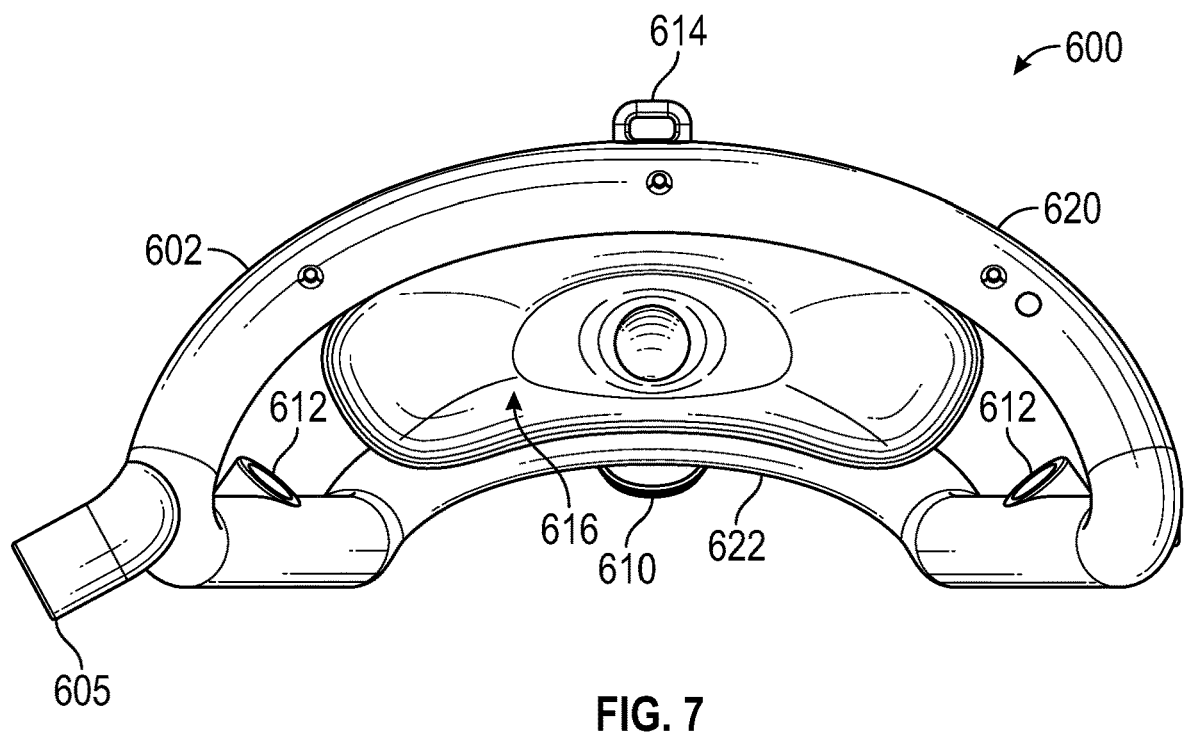
FIG. 7 is a front diagrammatic view of an evacuation dam system, according to at least one embodiment of the present inventive concept.
Figure 8:
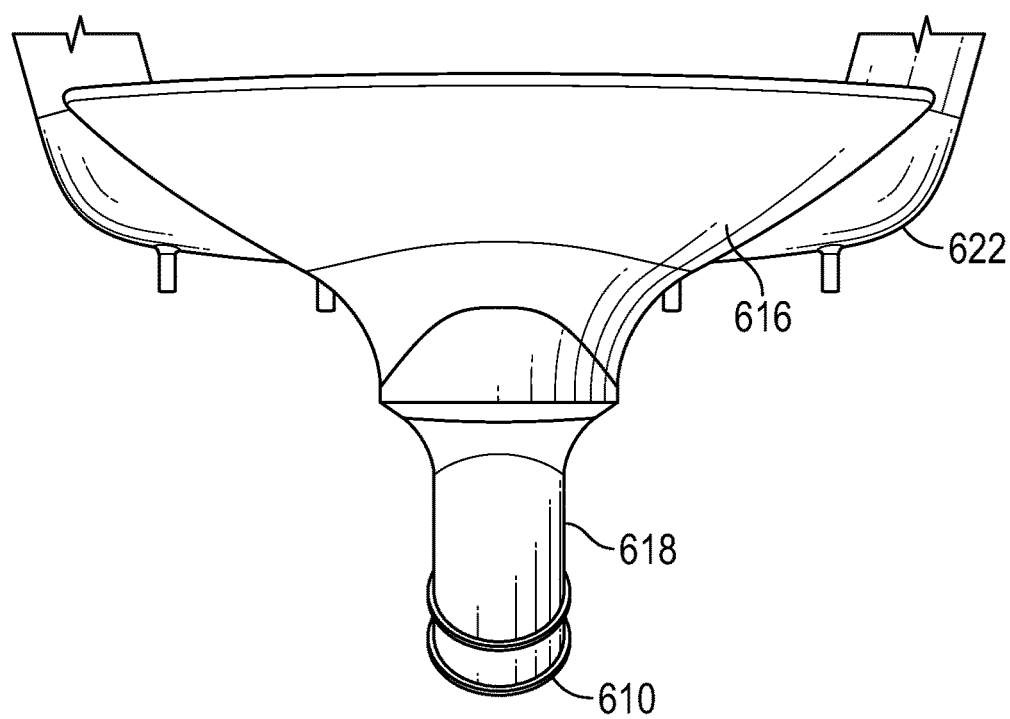
FIG. 8 is a diagrammatic view of a suction port of an evacuation dam system, according to at least one embodiment of the present inventive concept.
Figure 9:
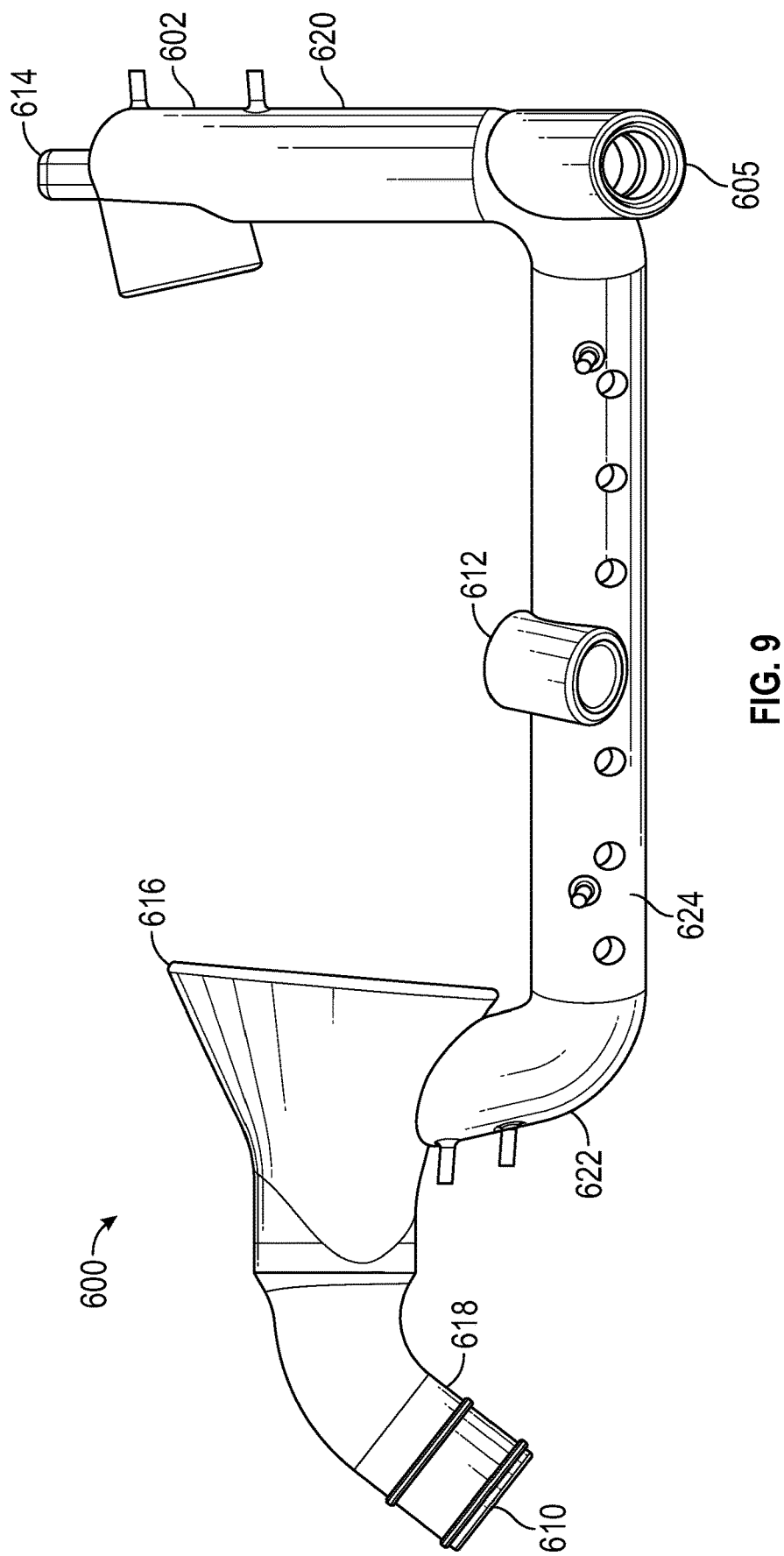
FIG. 9 is a right side elevational view of an evacuation dam system, according to at least one embodiment of the present inventive concept.

FIG. 6 illustrates a dual flow evacuation dam system, according to at least one embodiment of the present disclosure. FIG. 7 is a front elevational view of an evacuation dam system, according to at least one embodiment of the present disclosure. FIG. 8 illustrates a collection area and an evacuation connection of evacuation dam system, according to at least one embodiment of the present disclosure. FIG. 9 illustrates a right side elevational view of an evacuation dam system, according to at least one embodiment of the present disclosure. The evacuation dam system 600 can include an evacuation dam frame 602 defining a working area 604. The evacuation dam frame 602 can be operable to receive with a positive flow at least one positive flow inlet 605, and be operable to couple with a negative flow at a negative flow outlet 610.

The evacuation dam frame 602 can have one or more positive flow outlets 606 directed toward the working area 604 and one or more negative flow inlets 608 directed toward the working area 604 and substantially aligned with the one or more positive flow outlets 606, thereby defining a flow path 650 across the working area 604.

The evacuation dam system 600 can be further operable to couple with one or more saliva suction holders 612. The one or more saliva suction holders 612 can be operable to receive and/or couple with a saliva suction apparatus. The one or more saliva suction holders 612 can be positioned and/or arranged along at least a portion of the evacuation dam frame 602 to align the saliva suction apparatus with the working area 604 without interfering with the evacuation.

Figure 12:
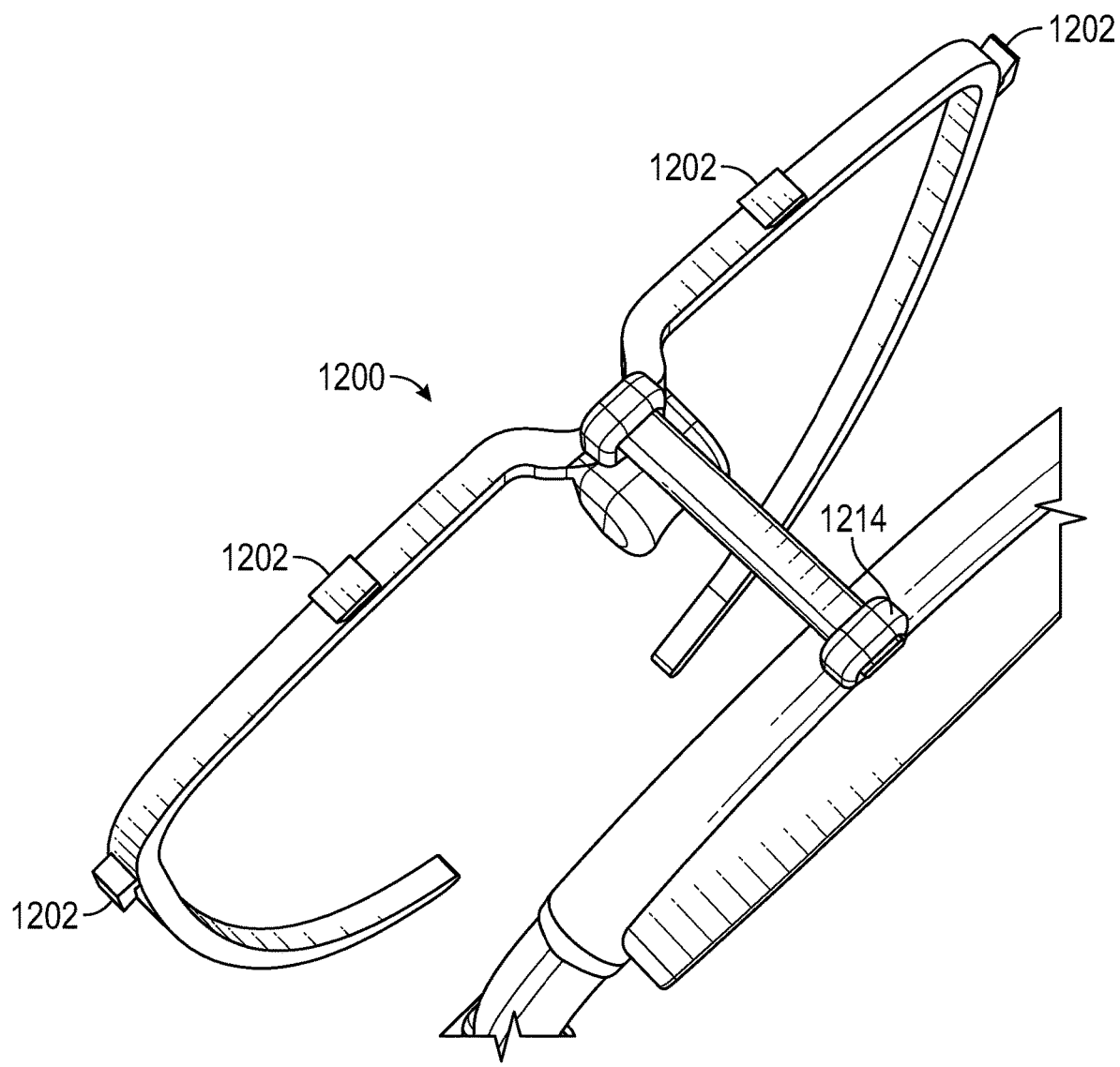
FIG. 12 is an isometric view of an eye protection system operably engaged with an evacuation dam, according to at least one embodiment of the present inventive concept.
Figure 13:
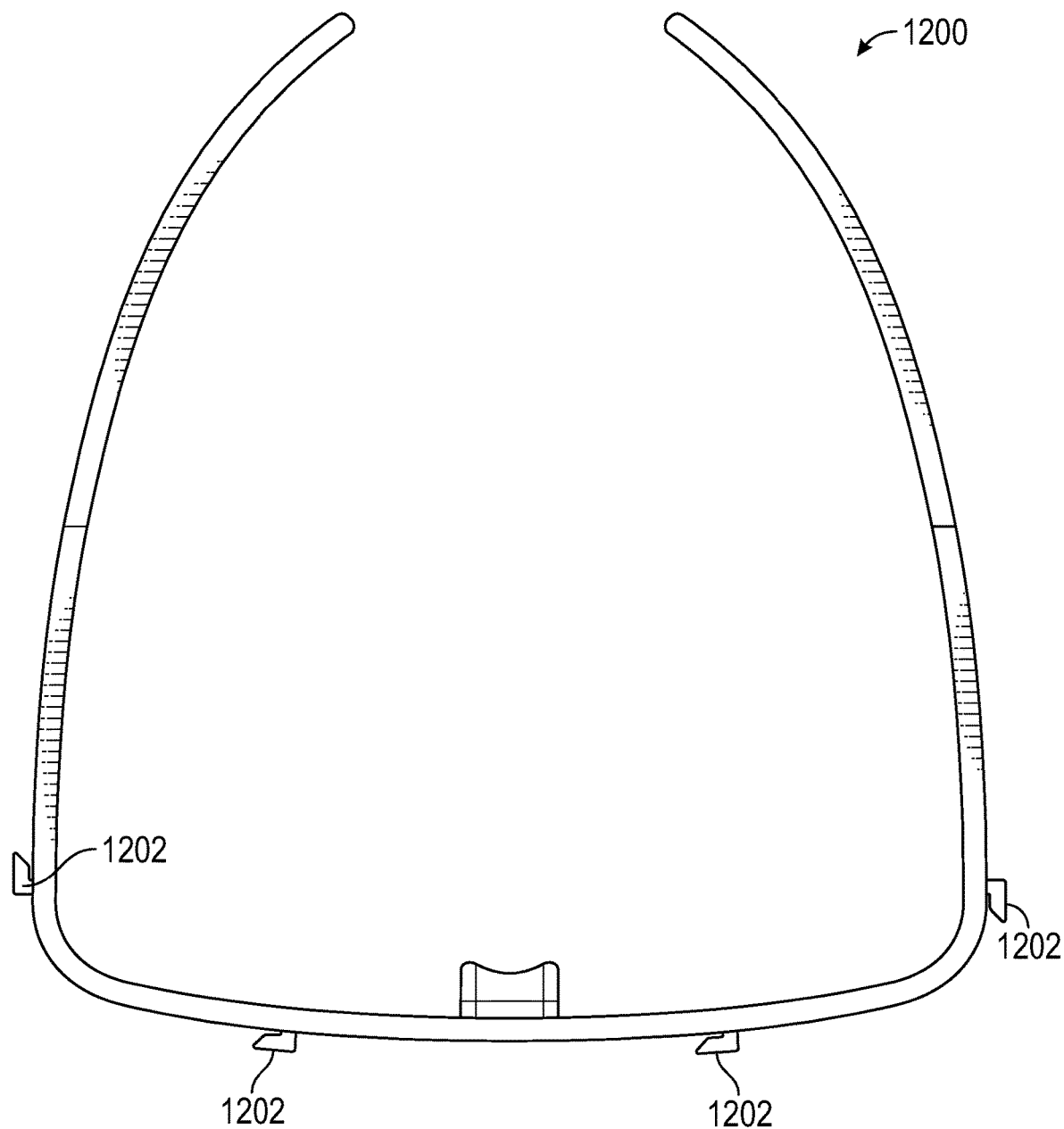
FIG. 13 is an elevational view of an eye protection system, according at least one embodiment of the present inventive concept.

The evacuation dam system 600 can further include an eye protection coupler 614 operable to receive and/or couple with an eye protection (shown in FIGS. 12 and 13).

As can be appreciated in FIG. 7, the one or more negative flow inlets 608 can be coupled with a convex collection area 616 and/or the central evacuation connection 618. The convex collection area 616 can be shaped and/or formed to direct the negative flow across the working area 604 and receive the positive flow from the one or more positive flow outlets 606.

As can further be appreciated FIG. 7, a top frame member 620 and/or a bottom frame member 622 can be arc-shaped, curved, or otherwise shaped to conform generally to a patient's face. While FIG. 8 illustrates a substantially arc-shaped top frame member 620 and/or bottom frame member 622 to conform to a face, it is within the scope of the present disclosure to shape and/or conform any of the top frame member 620, bottom frame member 622, and/or the side members 624, 626 to a corresponding body part or other feature for implementation of the evacuation dam 602 and/or the evacuation dam system 600.

As can be appreciated in FIG. 8 the convex collection area 616 and/or the central evacuation connection 618 can be arranged adjacent to the bottom frame member 622. The central evacuation connection 618 can allow for a single point connection between a negative pressure flow (e.g. vacuum) and the evacuation dam system 600. In at least one embodiment, the central evacuation connection 618 can be substantially centered along the bottom frame member 622. In other embodiments, the central evacuation connection 618 can be disposed at any point along the bottom frame member 622. While the present disclosure illustrates the central evacuation connection 618 coupled with the bottom frame member 622, it is within the scope of this disclosure to couple the central evacuation connection 618 with any of the top frame member 620, bottom frame member 622, the side members 622, 624 and/or combinations thereof.

The central evacuation connection 618 can be angled relative to a vertical axis to reduce actuation and/or pivotation of the evacuation dam system 600 on a patient's face. In at least one embodiment, the central evacuation connection 618 can be angled at approximately 45 degrees. In other embodiments, the central evacuation connection 618 can be flexible and/or adjustable to any desirable angle based on the patient, the hose arrangements, and/or the procedure. As can be further appreciated in FIG. 9, the side frame members 624, 626, according to an embodiment of the present disclosure, can form no part of the flow path for the positive flow and/or the negative flow. Therefore, the side frame members 624, 626 can be solid, hollow, and/or have ports formed thereon to reduce weight and/or aid in manufacturing.

The evacuation dam system 600 can be formed via additive manufacturing (e.g. 3-D printing), injection molded, cast, extruded, and/or other process. In some embodiments, the evacuation dam system 600 can be disposable for each patient. In other embodiments, the evacuation dam system 600 can be reusable and sterilized between patients using one or more of cleaning solutions and/or ultraviolet light sources.

Figure 10:
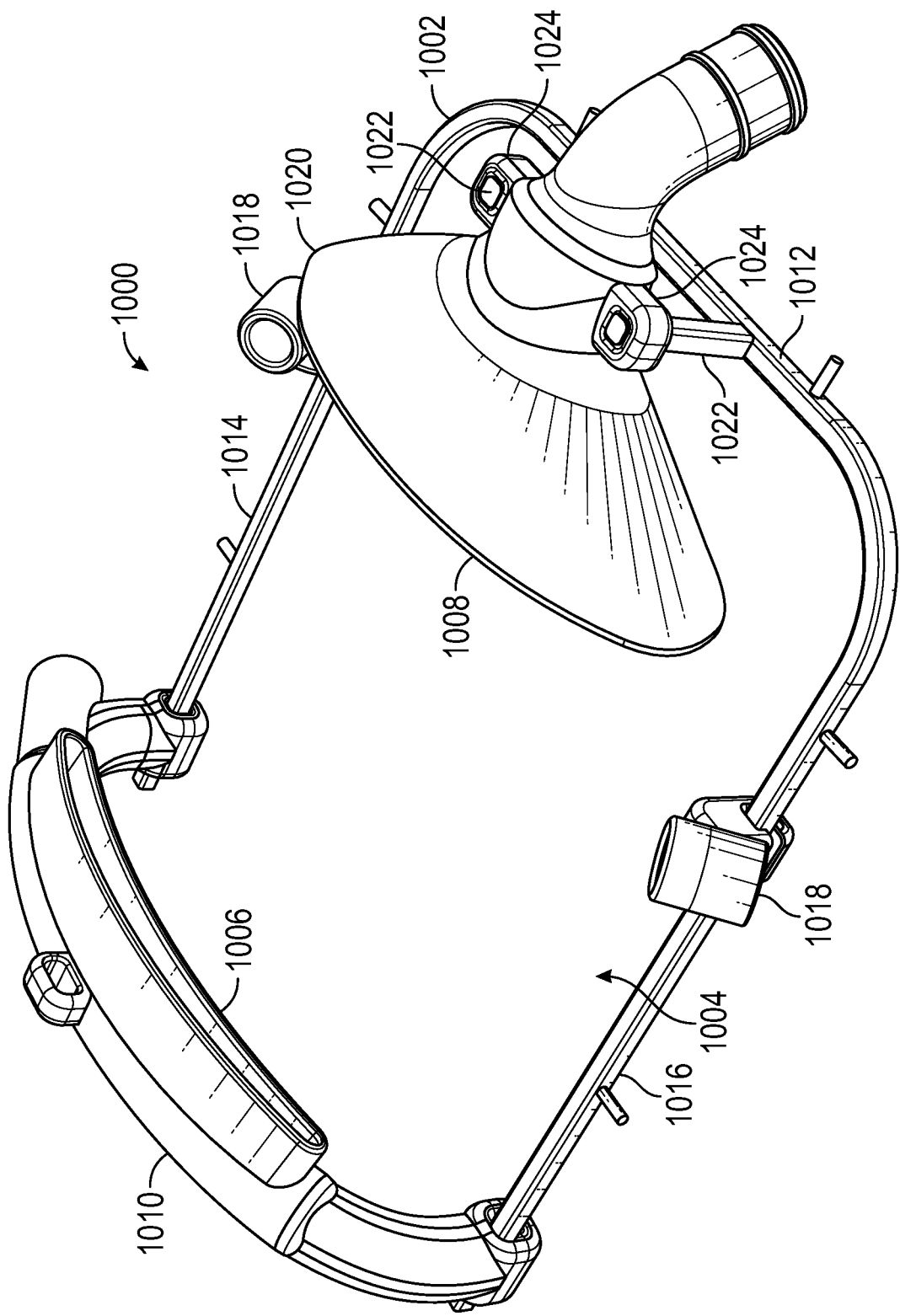
FIG. 10 is an isometric view of an adjustable evacuation dam system, according to at least one embodiment of the present inventive concept.

FIG. 10 illustrates an isometric view of an adjustable evacuation dam system, according to at least one embodiment of the present disclosure. An adjustable evacuation dam system 1000 can be implemented to customize the fit and function for each individual patient. A evacuation dam frame 1002 can form a working area 1004 with the evacuation dam frame 1002 operable to have one or more dimension adjustable, thereby adjusting the working area 1004. The evacuation dam system 1000 can include one or more positive flow outlets 1006 and one or more negative flow inlets 1008, as discussed above with respect to FIGS. 1-9.

The evacuation dam frame 1002 can include a top frame member 1010 a bottom frame member 1012, and side frame members 1014, 1016. The side frame members 1014, 1016 can be operable to slidingly couple with a portion of the top frame member 1010. The top frame member 1010 can slidingly engage with the side frame members 1014, 1016, thereby allowing a longitudinal length of the working area 1004 to be increased and/or shrunk depending on an individual patient's face and/or the procedure requirements. Further, one or more salvia suction holders 1018 can be slidingly engaged with one or more of the side frame members 1014, 1016 and disposed between the top frame member 1010 and the bottom frame member 1012. As can be appreciated in FIG. 10, the top frame member 1010 can be displaced along the side frame members 1014, 1016 toward the bottom frame member 1012 to reduce the working area 1004. While FIG. 10 illustrates the bottom frame member 1012 fixed relative to the side members 1012, 1014, it is within the scope of the present disclosure to have a slidingly engaged bottom frame member 1012 and/or a slidingly engaged top frame member 1010.

Figure 11:
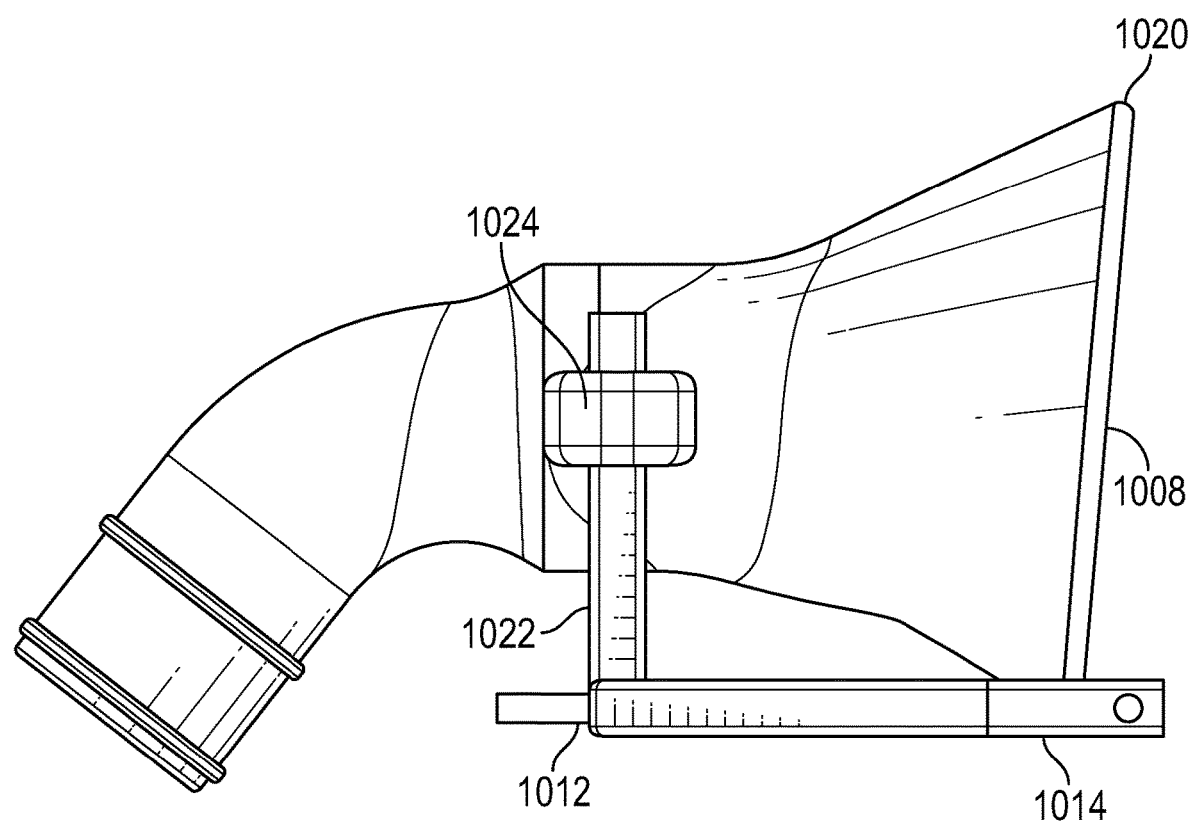
FIG. 11 is diagrammatic view of a suction port of an adjustable evacuation dam system, according to at least one embodiment of the present inventive concept.

FIG. 11 illustrates an adjustable collection area of an adjustable evacuation dam system, according to at least one embodiment of the present disclosure. An evacuation collection area 1020 can be slidingly coupled with the bottom frame member 1012 of the adjustable evacuation dam system 1000. The bottom frame member 1012 can have one or more adjustment posts 1022 extending vertically therefrom. The evacuation collection area 1020 can have one or more corresponding post couplers 1024 operable to receive the one or more adjustment posts 1022 therein. The evacuation collection area 1020 can then be slidingly adjusted in a vertical direction toward and/or away from the working area 1004 depending on the patient, procedure, and/or preference. In at least one embodiment, the evacuation collection area 1020 can pivot a predetermined number of degrees relative to the bottom frame member 1012 toward and/or away from the working area 1004.

FIG. 12 illustrates an isometric view eye protection of an evacuation dam system, according to at least one embodiment of the present disclosure. FIG. 13 illustrates a top elevation view of eye protection of an evacuation dam system, according to at least one embodiment of the present disclosure.

Eye protection 1200 can be coupled with an evacuation dam of the present disclosure. The eye protection 1200 can provide a patient with additional protection from the environment prior to, during, and/or after a procedure. The eye protection 1200 can engage with an eye protection coupler 1214 (as shown in FIGS. 6 and 10). In at least one embodiment, the eye protection 1200 can be slidingly engaged with an eye protection coupler 6 to adjust to an individual patient's face, body type, and/or respective procedure.

The eye protection 1200 can include one or more lens couplers 1202 operable to engage a lens. The one or more lens couplers 1202 can allow the lens to be replaced between patients and/or during a procedure, while allowing the eye protection 1200 to be sterilized and reused. In at least one embodiment, the eye protection 1200 can be implement with any number of lenses within varying shades of tint depending on the procedure and/or a patient's light sensitivity. The patient can have the opportunity to select a desire lens, which can then be coupled with the eye protection 1200 and/or the evacuation dam.

While preferred examples of the present inventive concept have been shown and described herein, it will be obvious to those skilled in the art that such examples are illustrative only. Further, it is within the scope of the present disclosure to combine one or more features of the illustrative examples disclose herein without deviating from the present disclosure. Numerous variations, changes, and substitutions will now occur to those skilled in the art without departing from the disclosure. It should be understood that various alternatives to the examples of the disclosure described herein can be employed in practicing the disclosure. It is intended that the following claims define the scope of the disclosure and that methods and structures within the scope of these claims and their equivalents be covered thereby.

What is claimed is:

1. An evacuation dam apparatus comprising:
   a frame having a top frame member, a bottom frame member, and two side frame members, the frame forming a working area;
   a plurality of ports adjacent the working area;
   an inlet fluidly coupled through a first portion of the frame with at least one of the plurality of ports; and
   an outlet fluidly coupled through a second portion of the frame with at least another one of the plurality of ports, the first portion of the frame being fluidically isolated from the second portion of the frame,
   wherein the evacuation dam is adapted to provide a fluid flow from the at least one of the plurality of ports across the working area to the at least another one of the plurality of ports, thereby forming a fluid flow path from inlet to the outlet.

2. The evacuation dam apparatus of claim 1, wherein the at least one of the plurality of ports includes at least one positive flow outlet port and the at least another one of the plurality of ports includes at least one negative flow inlet port.

3. The evacuation dam apparatus of claim 2, wherein the at least one positive flow outlet port is directional and substantially aligned with the at least one negative flow port.

4. The evacuation dam apparatus of claim 2, wherein the at least one negative flow port includes a convex collection area disposed around at least a portion thereof.

5. The evacuation dam apparatus of claim 1, wherein the frame includes a plurality of posts extending away from the working area.

6. The evacuation dam apparatus of claim 5, wherein each of the plurality of posts has a barb formed on a distal end thereof.

7. The evacuation dam apparatus of claim 1, wherein the frame has an eye protection coupler disposed thereon, the eye protection coupler configured to receive at least a portion of an eye protection apparatus.

8. The evacuation dam apparatus of claim 1, wherein the top frame member is slidingly engaged with the side members.

9. The evacuation dam apparatus of claim 1, wherein the outlet is slidingly engaged with the bottom frame member.

10. An evacuation dam system, comprising:
    an evacuation dam having a frame including a top frame member, a bottom frame member, and two side frame members;
    a working area defined by the frame;
    a positive flow inlet port configured to receive a positive pressure airflow therein;
    a positive flow outlet port adjacent the working area and fluidly coupled with the positive flow inlet port through a first portion of the frame;
    a negative flow inlet port adjacent the working area; and
    a negative flow outlet port configured to receive negative pressure airflow therein, the negative flow outlet port fluidly coupled with the negative flow inlet port through a second portion of the frame, the first portion of the frame being fluidically isolated from the second portion of the frame;
    wherein the evacuation dam system is configured to provide a fluid flow from at least the positive flow outlet port to the negative flow inlet port to form a fluid flow path across the working area.

11. The evacuation dam system of claim 10, wherein a positive pressure fluid flow path is formed in the top frame member.

12. The evacuation dam system of claim 10, wherein a negative pressure fluid flow path is formed in the bottom frame member.

13. The evacuation dam system of claim 10, where the at least one negative flow port includes a convex collection area disposed around at least a portion thereof.

14. The evacuation dam system of claim 13, wherein the convex collection area is coupled with the bottom frame member and is vertically displaceable relative to the bottom frame member.

15. The evacuation dam system of claim 10, further comprising an eye protection coupler configured to receive at least a portion of an eye protection apparatus, the eye protection coupler disposed on at least a portion of the frame.

16. The evacuation dam system of claim 10, further comprising a saliva suction holder coupled with a side frame member.

17. The evacuation dam system of claim 16, wherein the saliva suction holder is displaceable along a longitudinal length of the side frame member.

18. The evacuation dam system of claim 10, wherein the top frame member is slidingly displaceable along a longitudinal length of the side frame member, wherein changing a longitudinal length of the working area.

* * * * *